United States Patent
Ishitobi

(10) Patent No.: US 6,762,159 B2
(45) Date of Patent: Jul. 13, 2004

(54) POLYGLYCEROL FATTY ACID ESTER FOR DETERGENT AND DETERGENT CONTAINING THE SAME

(75) Inventor: Masahiko Ishitobi, Yokohama (JP)

(73) Assignee: Mitsubisi Chemical Corporation, Tokyo (JP)

( * ) Notice: Subject to any disclaimer, the term of this patent is extended or adjusted under 35 U.S.C. 154(b) by 0 days.

(21) Appl. No.: 09/978,651

(22) Filed: Oct. 16, 2001

(65) Prior Publication Data

US 2002/0123439 A1 Sep. 5, 2002

(30) Foreign Application Priority Data

Oct. 17, 2000 (JP) ........................................ 2000-316053

(51) Int. Cl.⁷ ............................ A61K 7/00; C11D 17/00
(52) U.S. Cl. ...................... 510/130; 510/424; 510/421; 510/432; 510/505
(58) Field of Search ................................ 510/130, 424, 510/432, 421, 505, 515

(56) References Cited

U.S. PATENT DOCUMENTS

| 5,589,099 A | * | 12/1996 | Baum ........................ 510/514 |
| 5,883,274 A | | 3/1999 | Shioguchi et al. |
| 6,294,515 B1 | * | 9/2001 | Baum ........................ 510/514 |

FOREIGN PATENT DOCUMENTS

| EP | 0 758 641 A1 | 2/1997 |
| JP | 06340896 A | 12/1994 |
| JP | 07145104 A | 6/1995 |
| JP | 08-217724 | 8/1996 |
| JP | 2000-287631 | 10/2000 |

* cited by examiner

Primary Examiner—Necholus Ogden
(74) Attorney, Agent, or Firm—Edwards & Angell, LLP; David G. Conlin; Lisa Swiszcz Hazzard

(57) ABSTRACT

The present invention relates to a detergent which comprises an aqueous solution containing not less than 2% by weight of a polyglycerol fatty acid ester and which is capable of remaining transparent for one week or more at 5° C.

8 Claims, No Drawings

POLYGLYCEROL FATTY ACID ESTER FOR DETERGENT AND DETERGENT CONTAINING THE SAME

BACKGROUND OF THE INVENTION

The present invention relates to a detergent with excellent transparency stability and a polyglycerol fatty acid ester composition suited for use for such a detergent.

Liquid detergents need to remain free from separating or precipitation of the constituents and be capable to maintain transparency stability, or the ability to remain transparent for a prolonged period of time, when placed under various environmental conditions in the market, especially in a cold district.

Japanese Patent Application Laid-Open (KOKAI) No. 6-340896 discloses a detergent containing an alkylene oxide adduct of a short-chain alcohol as a liquid detergent with improved transparency stability.

Polyglycerol fatty acid esters are a very mild surface active agent showing high performance in surface tension, emulsification, solubilization and foaming as well as high detergency, harmless to the human body and also little stimulant to the skin and hair, so that they are suited for cleaning foods, processed food materials, food producing equipment, tableware and such and actually used as a primary constituent of detergent compositions such as shampoo, body shampoo, cleanser, etc.

For instance, as a polyglycerol fatty acid ester with improved foaming ability, one containing not less than 70% of a fatty acid monoester obtained from an addition polymerization reaction of glycidyl and a fatty acid is known (Japanese Patent Application Laid-Open (KOKAI) No. 8-109153, EP 0758641 A1).

The hitherto known detergents containing a polyglycerol fatty acid ester, however, are still unsatisfactory in their ability to retain transparency, and the development of a detergent with high transparency stability has been desired.

SUMMARY OF THE INVENTION

In view of the above, the object of the present invention is to provide a transparent detergent which is capable of maintaining excellent transparency stability even if kept in storage for a long time, gives a good image as a commercial product, and is assured of high safety and thus anticipated to obtain high appraisal in the market.

As a result of the present inventors' earnest study, to solve the above problem, it has been found that such a detergent can be realized by using a polyglycerol fatty acid ester composition having a specific cloud point as a surface active agent.

In a first aspect of the present invention, there is provided a detergent which comprises an aqueous solution containing not less than 2% by weight of a polyglycerol fatty acid ester and which is capable of remaining transparent for one week or more at 5° C.

In a second aspect of the present invention, there is provided a detergent comprising a polyglycerol fatty acid ester composition whose cloud point as determined in an 8 wt % sodium sulfate solution in a concentration of 1% by weight is not lower than 40° C.

In a third aspect of the present invention, there is provided a detergent as defined in the above first aspect or second aspect which is to be used for foods.

In a fourth aspect of the present invention, there is provided a polyglycerol fatty acid ester composition whose cloud point as determined in an 8 wt % sodium sulfate solution in a concentration of 1% by weight is not lower than 40° C., and which composition contains not less than 0.1% by weight of soap.

The polyglycerol fatty acid ester compositions whose cloud point as determined in an 8% sodium sulfate solution in a concentration of 1% by weight is not lower than 40° C. are already known in the art as an emulsion stabilizer for foods, but their use for detergents is novel.

DETAILED DESCRIPTION OF THE INVENTION

The detergent according to the present invention is an aqueous solution which comprises not less than 2% by weight of a polyglycerol fatty acid ester and which is capable of remaining transparent for one week or more at 5° C.

The polyglycerol fatty acid ester (which may hereinafter be referred to as "PoGE") used in the present invention is an ester obtainable by reacting usually polyglycerol (which may hereinafter be referred to as "PoG") and a fatty acid. In the said polyglycerol fatty acid ester, the average degree of polymerization of the constituent polyglycerol is usually 4 to 20, preferably 8 to 14. The fatty acid forming another constituent of the ester is usually selected from the saturated or unsaturated fatty acids having 8 to 22 carbon atoms in the molecule, but it is preferably a saturated fatty acid having 8 to 14 carbon atoms in the molecule. Examples of such fatty acids include caprylic acid, capric acid, lauric acid and myristic acid, among which lauric acid is preferred. These fatty acids may be used as a combination of two or more depending on the purpose of use of the composition. The greater the content of the monoester, the more desirable. The average esterification degree is usually 1 to 1.5, preferably 1.

In the aqueous solution according to the present invention, usually water is used as medium, but it is possible to use a mixture of water and an alcohol such as ethanol, ethylene glycol, glycerin, propylene glycol or the like as medium. In case of using a mixture of water and an alcohol, their mixing ratio is not subject to any specific restrictions, but usually the content of water in the medium is not less than 70% by weight, preferably not less than 80% by weight, more preferably not less than 90% by weight.

The content of the polyglycerol fatty acid ester in the detergent is not less than 2% by weight. The content defined herein (not less than 2% by weight) is the content of the ester proper and does not indicate the content of the polyglycerol fatty acid ester composition which includes impurities such as the unreacted materials. The ester content is usually not more than 20% by weight, preferably not more than 15% by weight, more preferably not more than 10% by weight. Below 2% by weight, the content of the surface active agent (polyglycerol fatty acid ester) is too low to produce the desired detersive effect. It is to be also noted that supplementation of other surface active agent than a polyglycerol fatty acid for maintaining the detersive effect may prove detrimental to the safety of the composition. An ester content in excess of 20% by weight is also undesirable as it tends to induce precipitation.

"which is capable to remain transparent for one week or more at 5° C." means that the detergent can remain transparent for more than a week when it is allowed to stand at 5° C. immediately after its preparation. "Being transparent" means that the transmittance of the whole detergent is almost 100%, and such "transparent detergent" does not include one which forms a precipitate at the bottom of the container. The period in which the detergent can remain transparent is preferably not less than 50 days, more preferably not less than 100 days, even more preferably not less than 150 days. It is considered that if the preparation can remain transparent for more than a week at 5° C., it can well maintain high transmittance for a long time even in a cold district. On the other hand, in the case of a detergent which is not transparent from the time of its preparation or a detergent which can not keep transparency even for a week at 5° C., it is considered that such a detergent is liable to precipitate heavily at the bottom of the container if it is stored for a long time in a cold district. In such a case, the user may hold doubt about safety and cleaning ability of the detergent, and also the image of the detergent as a commercial product will be impaired from the aesthetic point of view.

The content of soap in the detergent of the present invention is not less than 0.01% by weight. A soap content of not less than 0.01% by weight is preferable as it helps better transparency stability of the detergent. This is attributable to the fact that since the soap molecules are trapped in the micells formed by the polyglycerol fatty acid ester, the negative charge carried by the soap molecules is given to the micells to generate a static repulsion which discourages aggregation or uniting of the micells with each other, suppressing the tendency of the composition to precipitate. The soap content is more preferably not less than 0.03% by weight, even more preferably not less than 0.1% by weight, still more preferably not less than 0.3% by weight. Usually, it is not more than 1% by weight, preferably not more than 0.5% by weight. "Soap" referred to in the present invention means a fatty acid alkaline metal salt. The constituent fatty acid of this fatty acid alkaline metal salt is usually the same as that of the above-mentioned polyglycerol fatty acid ester. The alkaline metal in the said fatty acid alkaline metal salt is usually potassium or sodium.

Polyglycerol fatty acid esters are produced usually by esterifying polyglycerol with a fatty acid in the presence of an alkaline catalyst. In this process, a fatty acid alkaline metal salt is formed as a by-product from a side reaction between the fatty acid and the alkaline catalyst. Also, since polyglycerol fatty acid esters are hard to purify, they are usually used in the non-purified form. Therefore, it is preferable in terms of process efficiency to produce a polyglycerol fatty acid ester composition containing the necessary amounts of a polyglycerol fatty acid ester and a fatty acid alkaline metal salt, and add this composition in the non-purified form. However, in case where the content of the fatty acid alkaline metal salt in the polyglycerol fatty acid ester composition is low, the fatty acid alkaline metal salt alone may be added separately. The constituent fatty acid of the separately added fatty acid alkaline metal salt may be the same as or different from that of the polyglycerol fatty acid ester, but it is preferably one which has 8 to 14, more preferably 8 to 12 carbon atoms in the molecule.

The detergent of the present invention may contain an alkaline metal salt of lactylic ester of fatty acid. It is considered that an alkaline metal salt of lactylic ester of fatty acid acts to discourage aggregation or unifying of micells like soap. The preferred content of the alkaline metal salt of lactylic ester of fatty acid in the detergent is usually not less than 0.01% by weight. In case where both of soap and alkaline metal salt of lactylic ester of fatty acid are contained in the detergent, the combined amount of the two is usually not less than 0.01% by weight. As the fatty acid and alkaline metal constituting the said alkaline metal salt of lactylic ester of fatty acid, the same fatty acid and alkaline metal mentioned in the above explanation of "soap" can be used.

The detergent according to the present invention can be produced by containing a polyglycerol fatty acid ester composition whose cloud point as determined in an 8 wt % sodium sulfate solution in a concentration of 1% by weight is not lower than 40° C.

Various chemical analytical methods have been used for the analysis of PoGE. For example, such factors as acid value, saponification value and hydroxy value were used for determining the degree of esterification or the amount of residual fatty acid, and the evaluation methods such as analysis of the ash have been used for determining the amount of soap or residual catalyst.

However, polyglycerol used as base material of PoGE, which is a polycondensate of glycerol and hard to purify, has a distribution of degrees of polymerization and contains not only a straight-chain polymer but also a branched or cyclic polymer. Therefore, its esterified product PoGE is a composition containing PoGE of various degrees of esterification with different PoG skeletons and unreacted PoG. PoGE may also contain soap, which is a by-product of the reaction between the alkaline catalyst used for the esterification reaction and the base material fatty acid, and may further contain unreacted fatty acid in case where the esterification reaction is incomplete or the fatty acid is used in excess of the stoichiometrical amount.

PoGE being a complex mixture as described above, it has been difficult to specify the synthetic properties of PoGE by the conventional chemical analytical techniques. For example, even if PoGE preparations are close or equal to each other in average esterification degree, they may drastically differ in properties such as emulsion stability, so that it has been impossible to know their properties sufficiently only by the conventional chemical analytical means such as determination of average esterification degree or unreacted PoG, thus producing impropriety in property evaluation. So, recently, the rating system by "cloud point" has come to be used for the specification of synthetic properties of polyglycerol fatty acid ester compositions.

Generally, "cloud point" is defined as a temperature at which there takes place two-phase separation of an ethylene oxide-derived nonionic surfactant solution by rise of temperature to make the solution heterogeneous, and the system using this phenomenon is well known as a method for evaluation of properties of polyoxyethylenic surfactants [Yushi Yogo Jiten (Glossary on Oils and Fats), compiled by Japan Oils and Fats Association, pub. by Saiwai Shobo]. Cloud point is sensitive to the structure and composition of polyglycerol fatty acid esters and even reflects fatty acid soap, so that it allows accurate recognition of the degree of hydrophilicity or the difference of composition. Further, with ease of determination, this system is the best method for determining the properties which characterize the polyglycerol fatty acid ester compositions. Therefore, cloud point is a more useful index for polyglycerol fatty acid ester compositions than HLB (hydrophilic-hydrophobic balance).

Since polyglycerols have many hydroxyl groups, cloud points of PoGE are generally higher than those of the polyoxyethylenic surfactants and may exceed the boiling point of water. In such a case, it is possible to make the determination easier to conduct by using an appropriate salt solution (Japanese Patent Application Laid-Open (KOKAI) No. 9-157386). Usually, the higher the hydrophilicity is, the higher becomes the cloud point, and even when the esterification rate is the same, a higher monoester content provides a higher cloud point.

In determination of cloud point, usually the polyglycerol fatty acid ester composition to be determined needs to be dissolved in a 1 to 30% sodium chloride or sodium sulfate solution and then subjected to the determination. The determination conditions are variable depending on the solubility of the sample to be determined, but in the case of the present invention, the polyglycerol fatty acid ester composition is first dispersed in an 8 wt % sodium sulfate solution to a concentration of 1% by weight to form a homogeneous aqueous solution. This solution is changed in temperature stepwise by 1 to 5° C. at one time in the arbitrary temperature range from 0° C. to 100° C. and allowed to stand for a while at a fixed temperature, and the temperature at which the polyglycerol fatty acid ester is separated in the form of oil drops, oil layer or gel to form a heterogeneous aqueous solution is measured. This temperature is what is called "cloud points" in the present invention. When the temperature is lower than 0° C. (as it becomes below the melting point of ice) or when the temperature exceeds 100° C. (as it becomes higher than the boiling point of water), it becomes difficult to make correct determination of cloud point.

The cloud point (as determined in an 8 wt % sodium sulfate solution in a concentration of 1% by weight) of the polyglycerol fatty acid ester composition used in the present invention is not lower than 40° C. The cloud point of "not lower than 40° C." means that it is in the range of 40 to 100° C. or may be higher than 100° C. in case where no heterogeneous aqueous solution is formed at 100° C. The higher the cloud point, the more preferable. When the cloud point is high, hydrophilicity of the polyglycerol fatty acid ester itself elevates correspondingly to discourage aggregation or uniting of the micells, suppressing the tendency for the composition to precipitate and consequently raising transparency stability of the aqueous solution. When the cloud point is below 40° C., hydrophobicity of the polyglycerol fatty acid ester elevates to lower its water solubility, reducing transparency stability of the aqueous solution. Cloud point is preferably not lower than 45° C., more preferably not lower than 50° C., even more preferably not lower than 80° C. Cloud point may be higher than 100° C. (in case where no heterogeneous aqueous solution is formed at 100° C.).

In the polyglycerol fatty acid ester composition used in the present invention, soap is contained in an amount of preferably not less than 0.1% by weight. If the soap content is not less than 0.1% by weight, the soap molecules are taken up in the micells formed by the polyglycerol fatty acid ester, affording the negative charge of the soap molecules to the micells to generate a static repulsive force which works to suppress aggregation or uniting of the micells with each other, thus discouraging precipitation of the composition. The soap content is more preferably not less than 0.3% by weight, even more preferably not less than 1% by weight, still more preferably not less than 3% by weight. Usually, the soap content is not more than 10% by weight, preferably not more than 5% by weight.

The average polymerization degree of polyglycerol constituting the polyglycerol fatty acid ester in the polyglycerol fatty acid ester composition is usually 4 to 20, preferably 8 to 14. The constituent fatty acid is usually selected from the saturated or unsaturated fatty acids having 8 to 22 carbon atoms in the molecule, but it is preferably a saturated fatty acid having 8 to 14 carbon atoms. Examples of such fatty acids are caprylic acid, capric acid, lauric acid and myristic acid, among which lauric acid is preferred. These fatty acids may be used as a combination of two or more depending on the purpose of use of the composition.

The ester content in the polyglycerol fatty acid ester composition is usually 10 to 60% by weight, preferably 20 to 50% by weight.

The PoGE composition having a cloud point of not lower than 40° C. used in the present invention can be produced by a direct esterification reaction of polyglycerol and a fatty acid, the reaction being carried out at 150 to 300° C., preferably 180 to 260° C., by using an alkaline catalyst in an amount of 0.001 to 3% by weight, preferably 0.001 to 1% by weight, based on the combined amount of the reaction materials (polyglycerol and fatty acid). As the alkaline catalyst, for instance, potassium carbonate, sodium carbonate, potassium hydroxide, sodium hydroxide and the like can be used. The reaction is usually carried out by supplying polyglycerol, a fatty acid and a catalyst to a stirrer type reactor and heating them to a prescribed temperature with stirring, with the generated water being discharged out of the reaction system. It is preferable that an inert gas such as nitrogen gas be passed through the gas phase region of the reactor during the reaction. The molar ratio of the fatty acid to polyglycerol in the feed is usually not greater than 1, preferably not greater than 0.8, and usually not less than 0.4.

A PoGE composition with a soap content of not more than 0.1% by weight and a cloud point of not lower than 80° C. can be produced by conducting the reaction for a long time at a relatively high temperature while confining the consumption of the alkaline catalyst in the esterification reaction to a small quantity. Specifically, in the direct esterification reaction of polyglycerol and a fatty acid, an alkaline catalyst is used in a very small quantity, i.e. 0.001 to 0.025% by weight, preferably 0.002 to 0.02% by weight, based on the combined amount of the reaction materials (polyglycerol and a fatty acid). When the amount of the alkaline catalyst used is less than 0.001% by weight, the esterification reaction does not proceed smoothly. On the other hand, when the amount of the alkaline catalyst exceeds 0.025% by weight, since the reaction temperature is high, there is a risk of incurring the undesirable phenomena such as tinting of the product, polymerization or cyclization of the starting polyglycerol, etc. The reaction temperature is usually 200 to 300° C. Preferably, the reaction temperature is kept at 200 to 240° C. at least until the fatty acid conversion reaches 70%, and thereafter the reaction temperature is further raised by 20 to 60° C. In this case, the reaction time after elevation of the reaction temperature is usually 2 to 6 hours. In the PoGE composition produced in the manner described above, usually soap is contained in an amount of not less than 0.1% by weight. The molar ratio of the fatty acid to polyglycerol in the feed is usually not greater than 1, preferably not greater than 0.8, and usually not less than 0.4.

A PoGE composition with a soap content of not less than 0.1% and a cloud point of not lower than 40° C. can be produced usually by carrying out the reaction for a short time at a relatively low temperature and using a relatively large quantity of an alkaline catalyst in the esterification reaction. Specifically, in a direct esterification reaction of polyglycerol and a fatty acid, an alkaline catalyst is used in an amount of 0.025 to 3% by weight based on the combined amount of the reaction materials (polyglycerol and fatty acid). When the amount of the alkaline catalyst used is less than 0.025% by weight, there is not provided a sufficient catalyst-derived soap content for obtaining low-temperature stability. On the other hand, when the amount of the alkaline catalyst exceeds 3% by weight, there is a risk of incurring the undesirable phenomena such as tinting of the product, polymerization or cyclization of the starting polyglycerol, etc. The reaction temperature is 160 to 240° C., preferably 180 to 220° C., and the reaction time is usually 3 to 10 hours. The molar ratio of polyglycerol to the fatty acid is usually not greater than 1, preferably not greater than 0.8, and usually not less than 0.4. For producing a PoGE composition with a soap content of not less than 0.1% by weight and a cloud point of not lower than 80° C., the amount of the alkaline catalyst is adjusted to be usually 0.3 to 3% by weight, preferably 0.3 to 1% by weight, more preferably 0.3 to 0.85% by weight based on the reaction materials in the above process.

In the detergent according to the present invention, a PoGE composition such as described above is added so that a necessary amount of a polyglycerol fatty acid ester will be contained in the detergent. Usually, the composition is added so that the said ester will be contained in an amount of 10 to 40% by weight, preferably 10 to 20% by weight in the detergent.

In case of adding soap in addition to the PoGE composition obtained from the esterification, either the soap may be added separately from the PoGE composition or they may be mixed together to prepare a PoGE composition with an increased soap content. The same applies where an alkaline metal salt of lactylic ester of fatty acid is used in place of soap.

In the detergent of the present invention, in order to allow it to manifest its maximum detergency, a chelating agent may be added. Use of a chelating agent conduces to not only preventing clouding of the hard water solution due to formation of scales in hard water containing calcium, magnesium, etc., but also maintaining detergency, foaming ability and fine touch of foams in hard water. The chelating agent used in the present is not specified; it is possible to use the conventionally used ones such as, for example, citrates, malates, tartarates, glutamates, pyrophosphates, polyacrylates, polymaleates, glucolates, nitrilotriacetates, acrylic acid-maleic anhydride copolymer salts, maleic anhydride-methylvinyl ether copolymer salts, maleic anhydride-olefin copolymer salts, maleic anhydride-methacrylic acid copolymer salts, maleic anhydride-tartaric acid condensate, zeolite, tripolyphosphates, ethylenediaminetetraacetic acid (EDTA), ethylenediamine and the like. Among these chelating agents, citrates, malates, tartarates, glutamates and pyrophosphates are preferred as they are safe to the human body, do not cause environmetal pollution, have high compatibility with PoGE used therewith and with water, alcohols, etc., used as detergent components, and are also helpful for producing high detergency, contaminant dispersability, foaming ability and a fine touch of foams. One or more of these chelating agents is (are) contained in an amount of 0.01 to 50% by weight, preferably 1 to 30% by weight in the detergent of the present invention.

Other substances selected arbitrarily from those commonly used in the conventional detergents may be also added in the detergent of the present invention within limits not prejudicial to the object of the invention. Examples of such additive substances include sodium polyoxyethylenealkylethersulfate, polyoxyethylene alkyl ether, polyoxyethylene alkylphenyl ether, sucrose fatty acid esters, monoglycerides, organic acid monoglycerides, sorbitan fatty acid esters, polyoxyethylenesorbitan fatty acid esters, fatty acid alkanol amides, surface active agents mild to the human body, such as carboxybetain type, imidasolium type, sulfobetain type and amino acid type surfactants, inorganic builders such as sodium carbonate, sodium sulfate, sodium chloride, magnesium sulfate and calcium chloride, fluidity improvers such as glycerin, ethanol, propylene glycol and polyethylene glycol, thickeners such as carboxymethyl cellulose and hydroxyethyl cellulose, perfumes, colorants, humectants, sterilizers, enzymes, anti-inflamatories, etc.

The detergent of the present invention can be obtained by dissolving the respective components homogeneously in an aqueous medium. The detergent of the present invention can be used for cleaning of foods, tableware, kitchen utensils, etc, and for cleaning of the skin and hair, or as various types of cleaning agents which have many opportunities of contact with the skin. It is especially suited for use as a cleaner for vegetables, fruit and foods such as broiler meat, fishes and shellfishes, etc.

The detergent of the present invention shows an excellent transparency stability even under the high-concentration conditions and can maintain a good image as a commercial product.

Further, the detergent of the present invention, beside high transparency stability mentioned above, also has high safety in use, is little stimulant to the skin, excels in cleaning performance such as detergency, foaming ability, hard water resistance, etc., and in the feel of use, and is also free of undesirable tinting or smelling, so that it is especially suited as a cleaner for foods, tableware and the like or as skin and hair cleaners such as shampoo, body shampoo, face cleanser, hand soap, etc. When used as a tableware cleaner, the detergent of the present invention is capable of expediting drying after rinsing, effecting finish free of waterdrop marks, and providing good gloss and sense of transparency of tableware after drying.

The detergent of the present invention can be easily produced by using a polyglycerol fatty acid ester composition having a specific cloud point.

EXAMPLES

The present invention is further illustrated by the following examples, but it should be understood that the following examples are merely intended to be illustrative and not to be construed as limiting the scope of the invention.

Preparation Example 1

Preparation of PoGE-A

First, 1,200 g of PoG (having an average polymerization degree of 10) was supplied to a 2-liter reactor equipped with a stirrer, a thermometer, a heating jacket, a gas feed opening and a reaction materials feed opening. Then lauric acid (99% purity) and a 10% sodium hydroxide solution were supplied to this reactor. The feed of lauric acid was adjusted so that the lauric acid/PoG molar ratio would become 0.7/1, while sodium hydroxide was supplied in an amount of 0.0025% by weight based on the total amount of PoG and lauric acid. With the reaction system placed in a stream of nitrogen under normal pressure, its internal temperature was raised to 240° C., and the mixture was reacted at this temperature for 3 hours. Then the internal temperature was further raised to 260° C., at which the mixture was additionally reacted for 4 hours. After the completion of the reaction, the internal temperature was lowered down to normal temperature to obtain a polyglycerol lauric acid ester (PoGE-A). The cloud point, PoGE content and soap content of the obtained reaction product were determined. The results are shown in Table 1.

Preparation Example 2

Preparation of PoGE-B

The same procedure as defined in Preparation Example 1 was conducted except that sodium hydroxide was supplied in an amount of 0.125% by weight, and that the reaction was carried out at 240° C. constantly for 7 hours to obtain a polyglycerol lauric acid ester (PoGE-B). The cloud point, PoGE content and soap content of the obtained reaction product were determined. The results are shown in Table 1.

Example 1

PoGE was dissolved in desalted water to prepare a 10% aqueous solution. The solution was kept at 5° C. and its state was observed at given time intervals. The results are shown in Table 1.

Example 2

The procedure of Example 1 was carried out by using PoGE-B in place of PoGE-A. The results are shown in Table 1.

Comparative Examples 1–5

The procedure of Example 1 was carried out by using the commercially available polyglycerol fatty acid esters PoGE-C, PoGE-D, PoGE-E, PoGE-F and PoGE-G, respectively, in place of PoGE-A. The results are shown in Table 1.

Preparation Example 3

A polyglycerol fatty acid ester composition (PoGE-A') was obtained in the same way as Example 1, and its cloud point, PoGE content and soap content were determined.

Preparation Example 4

To 100 g of PoGE-A' obtained in Example 3 was added 0.35 g of sodium laurate, and the mixture was heated and stirred at 80° C. to obtain a polyglycerol lauric acid ester composition (PoGE-H) containing 0.41% by weight of sodium laurate.

Preparation Example 5

To 100 g of PoGE-A' obtained in Example 3 was added 0.71 g of sodium laurate, and the mixture was heated and stirred at 80° C. to obtain a polyglycerol lauric acid ester composition (PoGE-I) containing 0.76% by weight of sodium laurate.

Preparation Example 6

To 100 g of PoGE-A' obtained in Example 3 was added 1.42 g of sodium laurate, and the mixture was heated and stirred at 80° C. to obtain a polyglycerol lauric acid ester composition (PoGE-J) containing 1.47% by weight of sodium laurate.

Preparation Example 7

The same procedure as defined in Example 1 was conducted except that the lauric acid/PoG molar ratio was changed to 0.5/1, that sodium hydroxide was supplied in an amount of 0.75% by weight based on the total amount of PoG and lauric acid, and that the reaction was carried out at 200° C. constantly for 5 hours to obtain a polyglycerol lauric acid ester composition (PoGE-K).

Preparation Example 8

The procedure of Preparation Example 7 was carried out by changing the lauric acid/PoG molar ratio to 0.7/1 to obtain a polyglycerol lauric acid ester composition (PoGE-L).

Examples 3–9

PoGE-A', B and H to L were dissolved respectively in desalted water to prepare the 10% aqueous solutions, these solutions were kept at 5° C. and their state was observed at given time intervals. The results are shown in Table 2.

TABLE 1

| | Example 1 | Example 2 | Comp. Example 1 | Comp. Example 2 | Comp. Example 3 | Comp. Example 4 | Comp. Example 5 |
|---|---|---|---|---|---|---|---|
| PoGE composition | | | | | | | |
| PoGE composition | PoGE-A | PoGE-B | PoGE-C | PoGE-D | PoGE-E | PoGE-F | PoGE-G |
| Soap[1] content (wt %) | 0.06 | 0.69 | 0.31 | 0.34 | 0.28 | 1.34 | 0.47 |
| PoGE content (wt %) | 44.1 | 44.1 | 69.3 | 70.5 | 51.0 | 65.1 | 65.2 |
| Cloud point (° C.) of 1% PoGE composition in 8% Na$_2$SO$_4$ solution | 87.5 | 52.5 | <25° C. | <25° C. | <25° C. | <25° C. | <25° C. |
| Appearance of 10% aqueous solution | | | | | | | |
| Immediately after preparation | Transparent | Transparent | Slightly turbid | Transparent | Turbid | Transparent | Slightly turbid |
| One week after preparation | Transparent | Transparent | Precipitated | Cloudy | Precipitated | Cloudy | Cloudy |
| One month after preparation | Transparent | Cloudy | Precipitated | Cloudy | Precipitated | Cloudy | Cloudy |

[1]Soap: sodium laurate

TABLE 2

| | Example 3 | Example 4 | Example 5 | Example 6 | Example 7 | Example 8 | Example 9 |
|---|---|---|---|---|---|---|---|
| PoGE composition | | | | | | | |
| PoGE composition | PoGE-A' | PoGE-H | PoGE-I | PoGE-J | PoGE-K | PoGE-L | PoGE-B |
| Soap[1] content (wt %) | 0.06 | 0.41 | 0.76 | 1.46 | 4.20 | 4.20 | 0.69 |
| PoGE content (wt %) | 44.1 | 44.0 | 43.8 | 43.5 | 24.0 | 34.7 | 44.1 |

TABLE 2-continued

|  | Example 3 | Example 4 | Example 5 | Example 6 | Example 7 | Example 8 | Example 9 |
|---|---|---|---|---|---|---|---|
| Cloud point (° C.) of 1% PoGE composition in 8% Na$_2$SO$_4$ solution | >90 | >90 | >90 | >90 | >90 | >90 | 52.5 |
| Period in which solution remained transparent (days) | 21 | 43 | 96 | 152 | >80 | >60 | 28 |

[1]) Soap: sodium laurate

The application is based on Japanese patent application No. JP 2000-316053 which was filed in Japan on Oct. 17, 2000 is incorporated by reference herein in its entirety.

What is claimed is:

1. A detergent which comprises an aqueous solution comprising a polyglycerol fatty acid ester composition, the aqueous solution containing not less than 2% by weight of a polyglycerol fatty acid ester, wherein the detergent is capable of remaining transparent for one week or more at 5° C., wherein the constituent polyglycerol of the polyglycerol fatty acid ester has an average degree of polymerization ranging from 4 to 20 and wherein the constituent fatty acid of the polyglycerol fatty acid ester has 8 to 14 carbon atoms, wherein the polyglycerol fatty acid ester composition has a cloud point of not lower than 40° C. as determined in an 8 wt % sodium sulfate solution in a concentration of 1 wt %, and wherein the polyglycerol fatty acid ester composition contains not less than 0.1% by weight of soap.

2. A detergent composition comprising a polyglycerol fatty acid ester composition whose cloud point as determined in an 8 wt % sodium sulfate solution in a concentration of 1% by weight is not lower than 40° C., wherein the constituent polyglycerol of the polyglycerol fatty acid ester has an average degree of polymerization ranging from 4 to 20 and wherein the constituent fatty acid of the polyglycerol fatty acid ester has 8 to 14 carbon atoms, and wherein the polyglycerol fatty acid ester composition contains not less than 0.1% by weight of soap.

3. A detergent according to claim 1 comprising a polyglycerol fatty ester composition whose cloud point as determined in an 8 wt % sodium sulfate solution in a concentration of 1% by weight is not lower than 80° C.

4. A detergent according to claim 2 comprising a polyglycerol fatty ester composition whose cloud point as determined in an 8 wt % sodium sulfate solution in a concentration of 1% by weight is not lower than 80° C.

5. A detergent according to claim 1 containing an alkaline metal salt of lactylic ester of fatty acids.

6. A detergent according to claim 2 containing an alkaline metal salt of lactylic ester of fatty acids.

7. A polyglycerol fatty acid ester composition whose cloud point as determined in an 8 wt % sodium sulfate solution is not lower than 40° C., and which composition contains not less than 0.1% by weight of soap, wherein the constituent polyglycerol of the polyglycerol fatty acid ester has an average degree of polymerization ranging from 4 to 20 and wherein the constituent fatty acid of the polyglycerol fatty acid ester has 8 to 14 carbon atoms.

8. A detergent which comprises an aqueous solution containing not less than 2% by weight of a polyglycerol fatty acid ester, which contains not less than 0.01% by weight of soap and which is capable of remaining transparent for one week or more at 5° C., wherein the constituent polylycerol of the polyglycerol fatty acid ester has an average degree of polymerization ranging from 4 to 20 and wherein the constituent fatty acid of the polyglycerol fatty acid ester has 8 to 14 carbon atoms.

* * * * *